United States Patent
Myhren et al.

(10) Patent No.: US 9,428,540 B2
(45) Date of Patent: Aug. 30, 2016

(54) FATTY ACID ESTERS OF GLUCOCORTICOIDS AS ANTI-INFLAMMATORY AND ANTI-CANCER AGENTS

(75) Inventors: Finn Myhren, Porsgrunn (NO); Marit Liland Sandvold, Porsgrunn (NO); Ole Henrik Eriksen, Oslo (NO); Steinar Hagen, Hagan (NO)

(73) Assignee: CLAVIS PHARMA ASA, Olso (NO)

( * ) Notice: Subject to any disclaimer, the term of this patent is extended or adjusted under 35 U.S.C. 154(b) by 1862 days.

(21) Appl. No.: 12/531,214

(22) PCT Filed: Mar. 13, 2008

(86) PCT No.: PCT/NO2008/000096
§ 371 (c)(1),
(2), (4) Date: Nov. 17, 2009

(87) PCT Pub. No.: WO2008/115069
PCT Pub. Date: Sep. 25, 2008

(65) Prior Publication Data
US 2010/0099654 A1    Apr. 22, 2010

(30) Foreign Application Priority Data
Mar. 20, 2007  (NO) .................................. 20071485

(51) Int. Cl.
*A61K 31/335* (2006.01)
*C07J 71/00* (2006.01)
*C07J 31/00* (2006.01)

(52) U.S. Cl.
CPC ........... *C07J 31/006* (2013.01); *C07J 71/0031* (2013.01)

(58) Field of Classification Search
USPC ....................................................... 514/463
See application file for complete search history.

(56) References Cited

U.S. PATENT DOCUMENTS

| | | | | |
|---|---|---|---|---|
| 3,557,162 | A | 1/1971 | Lens et al. | 260/397.45 |
| 4,335,121 | A | 6/1982 | Phillipps et al. | 424/241 |
| 6,762,175 | B2 * | 7/2004 | Myhren et al. | 514/180 |

FOREIGN PATENT DOCUMENTS

| | | |
|---|---|---|
| JP | 3-81286 | 4/1991 |
| JP | 5-132498 A | 5/1993 |
| WO | 0 170 642 A2 | 2/1986 |
| WO | WO 98/32718 | 7/1998 |
| WO | WO 02/08243 A1 | 1/2002 |
| WO | WO 03/066654 A1 | 8/2003 |
| WO | WO 2004/033478 A2 | 4/2004 |
| WO | WO 2008/115069 A3 | 9/2008 |

OTHER PUBLICATIONS

Tunek, A., "Reversible Formation of Fatty Acids Esters of Budesonide, an Antiasthma Glucocorticoid, in Human Lung and Liver Microsomes", Drug Metabolism and Disposition, 1997, vol. 24, No. 11, pp. 1311-1317.
Miller-Larsson et al., "Reversible Fatty Acid Conjugation of Budesonide. Novel Mechanism for Prolonged Retention of Topically Applied Steroid in Airway Tissue." Drug Metabolism and Disposition: The Biological Fate of chemicals, vol. 26, No. 7, Jul. 1998, pp. 623-630, XP002495986.
Teshima et al., "PEGylated Liposomes Loading Palmitoyl Prednisolone for Prolonged Blood Concentration of Prednisolone" Biological & Pharmaceutical Bulletin, vol. 29, No. 7, Jul. 2006, pp. 1436-1440, XP002495987.
Hashiguchi et al., "Evaluation of Topical Delivery of a Prednisolone Derivative Based upon Percutaneous Penetration Kinetic Analysis" Biological & Pharmaceutical Bulletin, vol. 21, No. 8, Aug. 1998, pp. 882-885, XP002495988.
Giraldi et al., "Chemical and Physicochemical Properties of the Pregna-1, 4-diene-3, 20-dione-11(beta, 17(alpha)-triol-21-stearoylglycolate" Arzenimittel-Forschung, vol. 16, No. 2, Feb. 1996, pp. 162-164, XP002495989.
Pifferi et al., "New Unsaturated Esters for Topical Antiphlogistic Use, Part 1: Synthesis and Spectroscopic Properties of Dexamethasone 21 Linoleate" Arzneimittel-Forschung, vol. 26, No. 1, 1976, pp. 7-10, XP002495990.
Homo-Delarche, "Glucocorticoid Receptors and Steroid Sensitivity in Normal and Neoplastic Human Lymphoid Tissues: A Review" Cancer Research, vol. 44, No. 2, Feb. 1984, pp. 431-437, XP002495991.
Fakih et al., "Glucocorticoids and Treatment of Prostate Cancer: A Preclinical and Clinical Review" Urology, vol. 60, No. 4, Oct. 2002, pp. 553-561, XP002495992.
Schoeller, "Die Antiphlogistische Wirksamkeit von Glucocorticoidestern bei lokaler Anwendung," Arzneimittel Eorschung Drug research, ECV Editio Cantor Verlagm Aulendorf, DE, vol. 10, No. 11, Jan. 1, 1960, pp. 921-923, XP002286160; and English translation thereof.

* cited by examiner

*Primary Examiner* — Barbara P Badio
(74) *Attorney, Agent, or Firm* — Fitzpatrick, Cella, Harper & Scinto

(57) ABSTRACT

The present invention relates to certain unsaturated fatty acid derivatives of therapeutically active glucocorticoides-fatty acid esters of glucocorticoids as anti-inflammatory and anti-cancer agents and pharmaceutical formulations containing them.

2 Claims, No Drawings

FATTY ACID ESTERS OF GLUCOCORTICOIDS AS ANTI-INFLAMMATORY AND ANTI-CANCER AGENTS

FIELD OF INVENTION

The present invention relates to certain unsaturated fatty acid derivatives of therapeutically active glucocorticoides and pharmaceutical formulations containing them. The said derivatives are referred to as "Compounds of formula (I)" in the present specification and claims. Compounds of formula (I) may be used in the treatment of cancerous and inflammatory diseases. Treatment of both haematological and solid cancers and steroide resistant cancers, asthma as well as steroide resistant inflammations and COPD are included.

TECHNICAL BACKGROUND

Glucocorticoids are extensively used in the treatment of inflammatory diseases, like asthma, rheumatoid arthritis, inflammatory bowel disease and autoimmune diseases. Glucocorticoids are also keystone drugs in the treatment of childhood acute lymphoblastic leukaemia (ALL) (1). Although their use in the treatment of chronic inflammatory diseases and cancer is common, the optimal efficacy is limited by inherent or acquired resistance to the drug. Steroid resistance is also a major problem in the management of patients with inflammatory bowel disease (2). A small number of asthmatic patients do not respond well or at all to corticosteroid therapy (3). Although the issue of glucocorticoid resistance may be less well explored in for instance rheumatoid arthritis than in haematological cancer, the latter two share common mechanisms of resistance, and strategies to overcome resistance after disease treatment will be of mutual interest (7).

The beneficial effects of glucocorticoids are thought to be mediated by suppression of inflammatory gene expression. They act by binding to a single receptor (glucocorticoid receptor, GR) localized in the cytosol of cells. Upon activation, GR translocates to the nucleus where it either switches on (transactivation) anti-inflammatory genes or turns off (transrepression) inflammatory genes (4). Gene induction requires GR dimerisation and DNA binding to specific GR response elements (GREs) located in the promoter region of responsive genes. Glucocorticoids may increase the transcription of genes coding for anti-inflammatory proteins, like lipocortin-1 and interleukin-10. The most striking effect of glucocorticoids is to inhibit the expression of multiple inflammatory genes (cytokines, enzymes, receptors and adhesion molecules). The proinflammatory cytokine granulocyte-macrophage colony-stimulating factor (GM-CSF) is an example. The glucocorticoides mediate this inhibitory effect by an interaction between activated GRs and activated transcription factors, such a nuclear factor-κB (NFκB) and activator protein-1 (AP-1), which regulates the inflammatory gene expression. GM-CSF plays a key role in inflammatory and autoimmune disease, and GM-CSF depletion is identified as a separate drug target for suppression of disease symptoms (8).

The use of the glucocorticoides is limited by serious side effects (5), due to their endocrine and metabolic actions, presumably mediated by induced transcriptional regulation of direct GR regulated target genes. The potential adverse effects reported include osteoporosis and suppression of the hypothalamic pituitary-adrenocortical axis, after systemic use, reduction of growth velocity in children, bone mineral loss, occular symptoms and skin changes after inhaled corticosteroid (6). The regulation of transactivation and transrepression, in both a tissue and pathway specific manner, may give improvement of therapeutic index and open for highly selective new corticosteroids (6) with higher therapeutic effect against inflammation or cancer and less side effects due to lower transcriptional regulation of the GR regulated genes of importance for the side effects.

Furthermore, the mechanistic basis also for the anti-cancer effects of glucocorticoids do involve an interaction with GR and it's target genes controlling the expression of cell death/apoptosis proteins.

The cell lines U937 and THP1 are human monocytic/macrophage cells and represent cell line model systems used to test products for anti-inflammatory and anti-cancer activity, the cell lines are also relevant for glucocorticoid resistance, as they are refractory to growth inhibition by dexamethasone and prednisolone (7).

The commonly assigned publication WO98/32718 describes adrenocorticosteroids which may be derivatised with lipophilic groups. Among the compounds mentioned are betamethasone, dexamethasone, and beclomethasone. These derivatised compounds are used to treat inflammation.

Fatty acid conjugates of budesonide, more specifically budesonide oleate, palmitate, linoleate, palmitoleate, and arachidonate have been described. These conjugates are formed during the treatment of inflammation, more specifically asthma, but the fatty acid conjugates of the steroids mentioned are said to be pharmacologically inactive lipoidal conjugates (12).

DESCRIPTION OF THE INVENTION

The present invention has surprisingly shown that certain unsaturated fatty acid derivatives of glucocorticoids demonstrate new and surprising therapeutic activities. A great number of said derivatives constitute new chemical compounds not previously described. The derivatives of the present invention have demonstrated increased activity and fewer side effects compared to previously described glucocorticoid derivatives and they have shown activity in steroid resistant systems.

It is known that glucocorticoids have a position in the treatment of cancerous disease and inflammation. Inherent or acquired resistance to treatment with glucocorticoids is well known. It has been reported that the human U937 and THP1 monocytic/macrophage cells represent a cell line model system characterized by inherent resistance to the glucocorticoids dexamethasone and prednisolone (7). We have confirmed these findings and in addition shown that the cells are cross-resistant to the highly potent steroid fluticasone propionat with no activity seen up to 100 μM.

As demonstrated in the examples we have surprisingly found high anti-proliferative activity of glucocorticoid fatty acid derivatives in these resistant cell lines. This finding enables treatment of diseases resistant to treatment with known glucocorticoids.

We have surprisingly found an increased anti-inflammatory activity combined with a less pronounced activation of genes relevant for side effects with the glucocorticoid fatty acid derivatives. A 22 fold more potent inhibition of the cytokine GM-CSF release has been observed for the fluticasone elaidic acid derivative compared to fluticasone pro pionate in activated lung cells. At the same time, 7 fold decrease in side effects is found. The side effects are represented by activation of GRE elements. The gene activation is 85% less for the steroid derivative in this system where activation is a measure for side effects. These results increase the relative therapeutic index 154 fold.

The present invention thus relates to compounds of formula (I)

[Chemical structure of formula (I) showing steroid skeleton with substituents $R_4O$, $R_1$, $R_2$, $R_3$, $X_1$, $X_2$]

wherein:

$X_1$ and $X_2$ independently represent H or F;
$R_1$ represents OH, $OCH_2CH_3$, $OCH_2Cl$, $SCH_2F$, $CH_2OCOCH(CH_3)_2$, $CH_2$—O—$R_4$ or O—$R_4$;
$R_2$ represents OCOEt, $OCOCHCl_2$, $OCO_2CH_2CH_3$ or O—$R_4$;
$R_3$ represents H, $CH_3$ or OH; or
$R_2$ and $R_3$, together with the carbon atoms to which they are bonded, form a 2-$R_5$, $R_6$-1,3-dioxoloane ring, wherein $R_5$ and $R_6$ independently represent H, $C_1$-$C_6$ alkyl or $C_3$-$C_6$ cycloalkyl;
$R_4$ represents H or a $C_8$-$C_{24}$ acyl group of the general formula $$CH_3\text{—}(CH_2)_k\text{—}(CH\text{=}CH\text{—}CH_2)_l\text{—}(CH\text{=}CH)_m\text{—}(CH_2)_n\text{—}CO \quad (II)$$

wherein k is an integer from 0 to 10, l is an integer from 0 to 6, m is an integer from 0 to 1, and n is an integer from 2 to 7;
with the following provisios:
 when $X_1$ is F, $X_2$ is not H;
 at least one acyl group of the general formula (II) is present in the compound; and
 the compound of formula (I) is not one of the following compounds: budesonide oleate, budesonide palmitate, budesonide linoleate, budesonide palmitoleate and budesonide arachidonate;
or a pharmaceutically acceptable salt thereof.

In a preferred embodiment of the invention the compound of formula (I) is a compound wherein
$X_1$ and $X_2$ both represent F;
$R_1$ represents $SCH_2F$;
$R_2$ represents OCOEt or O—$R_4$;
$R_3$ represents $CH_3$;
$R_4$ represents H or a $C_8$-$C_{24}$ acyl group of the general formula $$CH_3\text{—}(CH_2)_k\text{—}(CH\text{=}CH\text{—}CH_2)_l\text{—}(CH\text{=}CH)_m\text{—}(CH_2)_n\text{—}CO \quad (II)$$

wherein k is an integer from 0 to 10, l is an integer from 0 to 6, m is an integer from 0 to 1, and n is an integer from 2 to 7;
with the provisio that at least one acyl group of formula (II) is present in the compound, or a pharmaceutically acceptable salt thereof.

Another embodiment of the invention is a compound of formula (I) wherein
$X_1$ and $X_2$ both represent H;
$R_1$ represents $CH_2$—O—$R_4$;
$R_2$ and $R_3$, together with the carbon atoms to which they are bonded, form a 2-$R_5$, $R_6$-1,3-dioxolane ring, wherein $R_5$ and $R_6$ represent H, $C_1$-$C_6$-alkyl or $C_3$-$C_6$-cycloalkyl;
$R_4$ represents H or a $C_8$-$C_{24}$ acyl group of the general formula $$CH_3\text{—}(CH_2)_k\text{—}(CH\text{=}CH\text{—}CH_2)_l\text{—}(CH\text{=}CH)_m\text{—}(CH_2)_n\text{—}CO \quad (II)$$

wherein k is an integer from 0 to 10, l is an integer from 0 to 6, m is an integer from 0 to 1, and n is an integer from 2 to 7;
with the provisio that at least one acyl group of formula (II) is present in the compound, or a pharmaceutically acceptable salt thereof.

A further embodiment of the invention is a compound of formula (I) wherein
$X_1$ and $X_2$ both represent F;
$R_1$ represents O—$R_4$;
$R_2$ represents O—$R_4$;
$R_3$ represents $CH_3$;
$R_4$ represents H or a $C_8$-$C_{24}$ acyl group of the general formula $$CH_3\text{—}(CH_2)_k\text{—}(CH\text{=}CH\text{—}CH_2)_l\text{—}(CH\text{=}CH)_m\text{—}(CH_2)_n\text{—}CO \quad (II)$$

wherein k is an integer from 0 to 10, l is an integer from 0 to 6, m is an integer from 0 to 1, and n is an integer from 2 to 7;
with the provisio that at least one acyl group of formula (II) is present in the compound or a pharmaceutically acceptable salt thereof.

Preferred compounds according to the present invention are exemplified by, but not limited to, the following compounds

[Chemical structure of a budesonide derivative with long-chain unsaturated acyl ester]

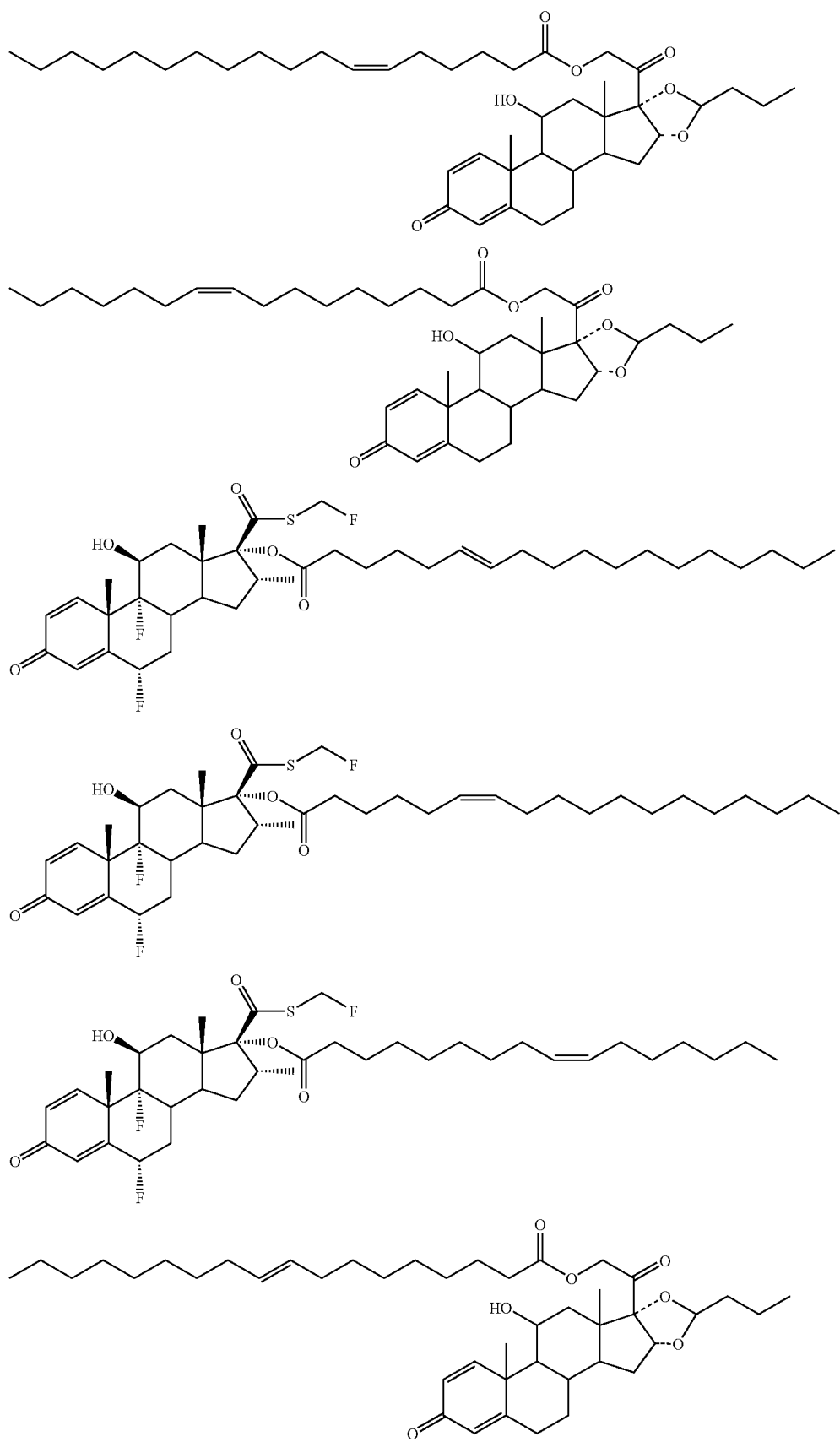

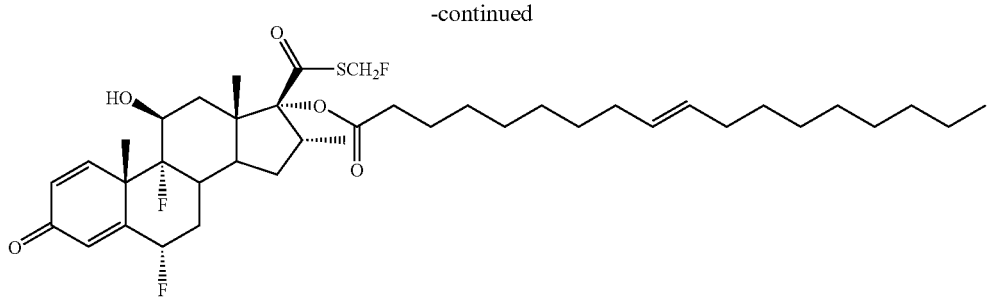

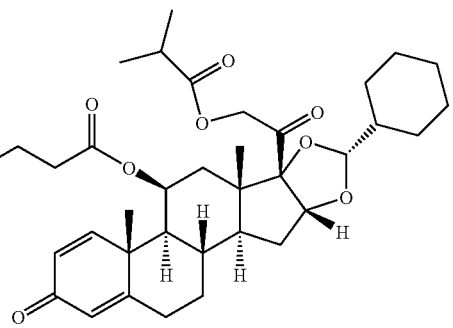

The compounds of formula (I) may be used for the treatment of diseases. More specifically the compounds of formula (I) may be used for the treatment of cancers. Cancers in this connection include haematological cancers, solid cancers and steroid resistant cancers. The compounds may also be used for the treatment of inflammation. More specifically the compounds are well suited for the treatment of steroid resistant inflammations. The compounds of formula (I) may also be used for the treatment of COPD (chronic obstructive pulmonary disease).

The compounds according to the present invention cause less side effects than the basic steroids and have a more specific anti-inflammatory activity.

The compounds of the present invention will normally, but not necessarily, be formulated into pharmaceutical compositions prior to administration to a patient. In another aspect the invention is accordingly directed to pharmaceutical compositions comprising a compound of the invention and one or more pharmaceutically acceptable excipients.

The said excipients are chosen according to the desired pharmaceutical form and the desired mode of administration. Said excipients together with a compound of formula (I) according to the invention will typically be formulated in a dosage form adapted for administration to the patient by the intended route of administration. Dosage forms thus include forms adapted for: (a) inhalation administration such as aerosoles, solutions and dry powders; (b) topical administration such as creams, lotions, pastes, ointments, solutions, sprays and gels; (c) intravenous administration such as sterile solutions, suspensions and powders for reconstitution; (d) oral administration such as tablets, capsules, pills, powders, syrups, elixirs, suspensions, solutions, emulsions and sachets. The compound of formula (I) may also be administered as eyedrops.

Suitable pharmaceutically acceptable excipients will vary depending of the particular dosage form. Pharmaceutically acceptable excipients include, inter alia, the following: diluents, lubricants, fillers, disintegrating agents, solvents, wetting agents, suspending agents, emulsifiers, granulating agents, coating agents, binders, flavoring agents, flavor masking agents, sweeteners, plasticizers, viscosifying agents, antioxidants, stabilizers, surfactants and buffering agents. Certain excipients may serve more than one function.

Suitable diluents and fillers include lactose, sucrose, dextrose, mannitol, sorbitol, potato starch, corn starch, pregelatinized starch, cellulose and derivatives thereof. Suitable binders include starch, gelatine, acaica, sodium alginate, alginic acid, tragacant, guar gum, povidone and cellulose and derivatives thereof. Suitable disintegrants include sodium starch glycolate, alginic acid, crospovidone, and sodium carboxymethyl cellulose.

The compounds of formula (I) may also be coupled to biodegradable polymers for controlled release of a drug.

The pharmaceutical compositions according to the invention may be prepared using methods and techniques known to those skilled in the art.

An aspect of the present invention is thus compounds of formula (I) for the treatment of cancer in accordance with claims 9-12.

Another aspect of the invention is the use of the compound of formula (I) for the preparation of pharmaceutical compositions for the treatment of the indicated diseases in accordance with claims 14-21.

The compounds of formula (I) may be prepared as exemplified below.

11β-Elaidic Acid Ester of Fluticasone Propionate

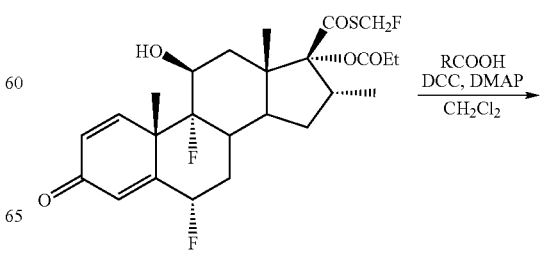

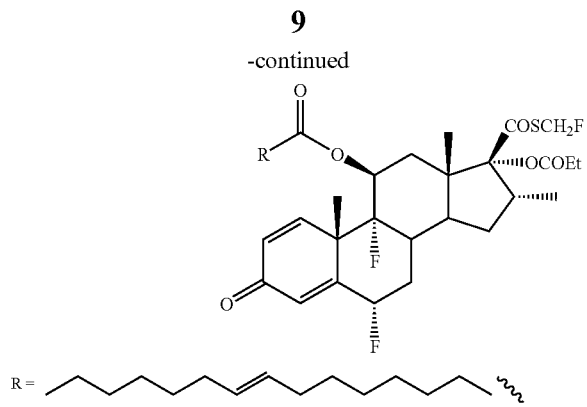

R = [structure shown]

To a solution of fluticasone propionate (1.02 g, 2.04 mmol) in dichloromethane (35 ml) was added elaidic acid (576 mg, 2.04 mmol) followed by 4-(dimethylamino)pyridine (249 mg, 2.04 mmol) and 1,3-dicyclohexylcarbodiimide (421 mg, 2.04 mmol). The resulting solution was stirred for 24 h at which time TLC revealed a significant amount of starting material left. The mixture was concentrated in vacuo (~10 ml solution) and stirred for an additional 140 h. The mixture was further concentrated in vacuo and purified by flash chromatography on silica gel eluting with Hexane/EtOAc (3:1) to give 1.23 g (79%) of the desired compound as a colourless oil.

6α,9α-Difluoro-11β,17α-dihydroxy-16α-methyl-3-oxoandrosta-1,4-diene-17β-carboxylic acid

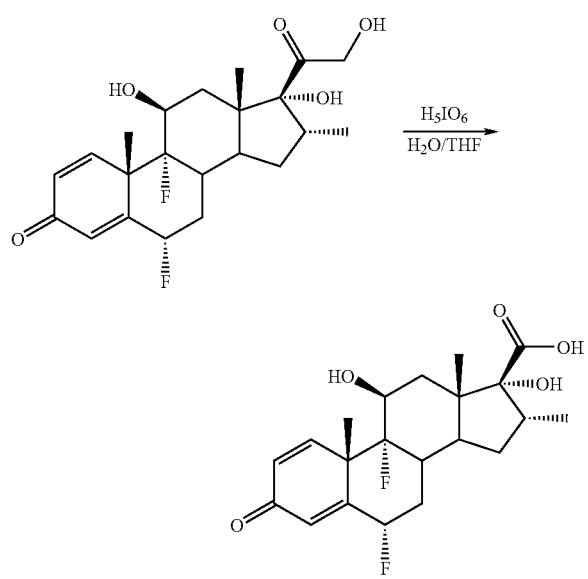

To a suspension of flumethasone (1.19 g, 2.9 mmol) in tetrahydrofuran (11 ml) was added a solution of periodic acid (2.25 g, 9.9 mmol) in water (5.3 ml). The resulting solution was stirred at RT for 1 h. The tetrahydrofuran was removed in vacuo to leave an aqueous suspension which was filtered, and the solid washed with water and dried to give 1.17 g (100%) of the title compound as a colourless solid.

6α,9α-Difluoro-16α-elaidoyloxy-11β-hydroxy-16α-methyl-3-oxoandrosta-1,4-diene-17β-carboxylic acid

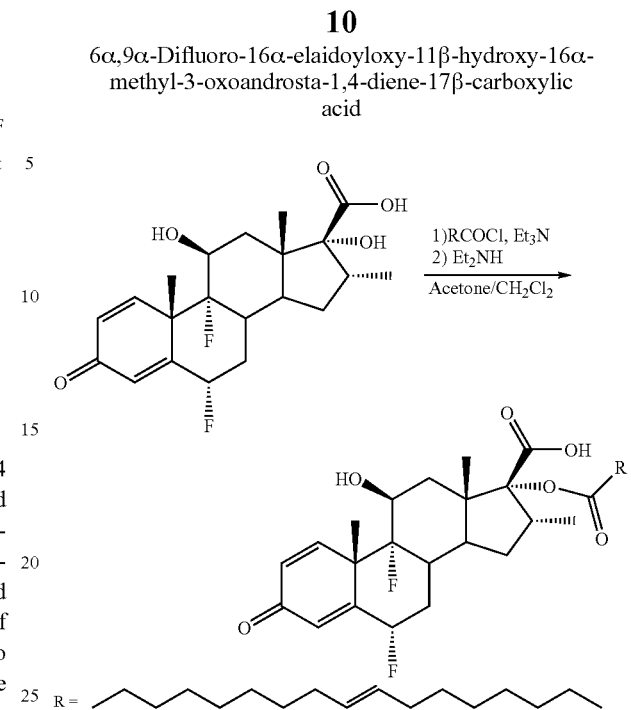

R = [structure shown]

A solution of 6α,9α-difluoro-11β,17α-dihydroxy-16α-methyl-3-oxoandrosta-1,4-diene-17β-carboxylic acid (1.22 g, 3.1 mmol) and triethylamine (0.72 g, 7.1 mmol) in acetone (25 ml) was added elaidoyl chloride in dichloromethane (10 ml). The elaidoyl chloride had been prepared from elaidic acid (2.0 g, 7.1 mmol), oxalyl chloride (2.6 ml, 30 mmol) and DMF (catalytic amount) in toluene (45 ml) by stirring at ambient temperature for 17 h and then evaporated to dryness. The resulting mixture was stirred for 2 h at RT, treated with diethylamine (0.97 ml, 9.2 mmol) and the resulting solution stirred an additional 1.5 h at RT. 1 M HCl was then added and the mixture extracted with dichloromethane (3×50 ml). The combined organic extracts were dried (Na₂SO₄), filtered and removed in vacuo. The crude product was dissolved in EtOAc, added hexane and put in the refrigerator overnight. The off-white solid (2.07 g, containing some N,N-diethyl amide) obtained was collected by filtration, dried and used directly in the next step. Some of the title compound (170 mg) was purified by flash chromatography on silica gel eluting with hexane/EtOAc (4:1) followed by hexane/EtOAc/AcOH (100:100:1) to give 123 mg (72%) as a white solid.

6α,9α-Difluoro-17β-(N,N-dimethylcarbamoylthio)carboyl-16α-elaidoyloxy-11β-hydroxy-16α-methyl-3-oxoandrosta-1,4-diene

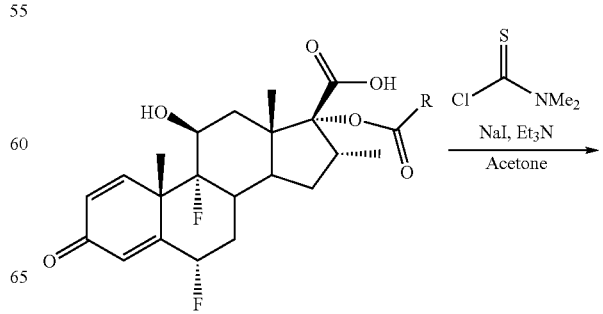

-continued

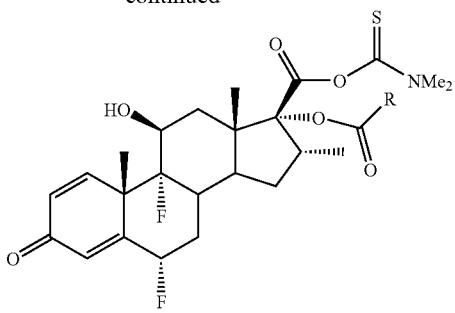

A solution of 6α,9α-difluoro-16α-elaidoyloxy-11β-hydroxy-16α-methyl-3-oxoandrosta-1,4-diene-17β-carboxylic acid (1.9 g, 2.9 mmol) and N,N-dimethylthiocarbamoyl chloride (0.71 g, 5.8 mmol) in acetone (40 ml) at RT was treated sequentially with triethylamine (0.58 g, 5.8 mmol), anhydrous sodium iodide (0.43 g, 2.9 mmol) and water (0.19 ml, 10% w/w with the steroid). The solution was stirred for 18 h, added water (100 ml) and EtOAc (100 ml), and the phases separated. The organic phase was washed with 1 M HCl, a 5% aqueous solution of sodium hydrogen carbonate, water, dried (Na$_2$SO$_4$), filtered and removed in vacuo. Flash chromatography on silica gel eluting with hexane/EtOAc (3:2) afforded 1.55 g (~70%, two steps) of the title compound as a yellow solid.

6α,9α-Difluoro-16α-elaidoyloxy-11β-hydroxy-16α-methyl-3-oxoandrosta-1,4-diene-17β-carbothioic acid

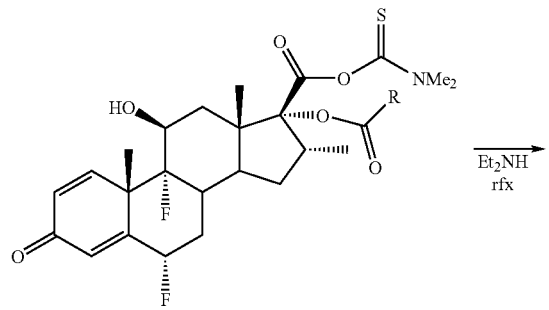

A solution of 6α,9α-difluoro-17β-(N,N-dimethylcarbamoylthio)carboyl-16α-elaidoyloxy-11β-hydroxy-16α-methyl-3-oxoandrosta-1,4-diene (1.55 g, 2.1 mmol) in diethylamine (16 ml) was refluxed for 3 h. The solution was cooled to ambient temperature, poured into cold 3 M HCl (150 ml) and extracted with EtOAc (2×150 ml). The combined organic extracts were washed with water, and brine prior to drying (Na$_2$SO$_4$), filtration and evaporation in vacuo. The crude product (1.35 g, off-white solid) was used directly in the next step.

S-Chloromethyl 6α,9α-difluoro-16α-elaidoyloxy-11β-hydroxy-16α-methyl-3-oxoandrosta-1,4-diene-17β-carbothioate

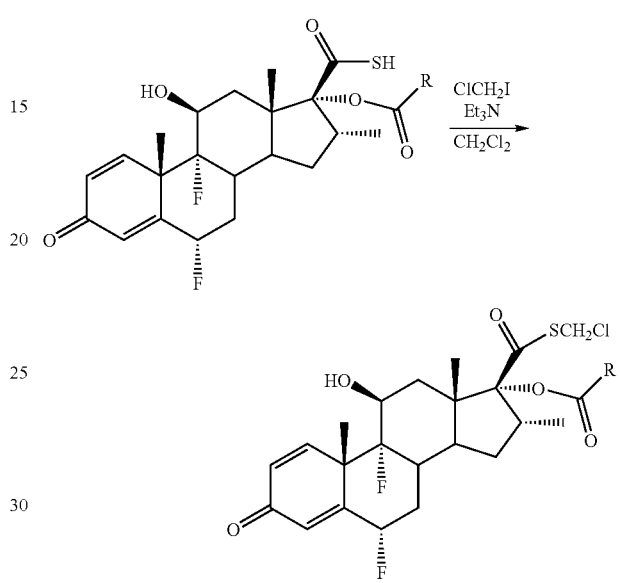

A stirred solution of 6α,9α-difluoro-16α-elaidoyloxy-11β-hydroxy-16α-methyl-3-oxoandrosta-1,4-diene-17β-carbothioic acid (1.35 g, 2 mmol) in dichloromethane (40 ml) was added triethylamine (0.28 ml, 2 mmol) followed by chloroiodomethane (0.56 ml, 8 mmol). The resulting solution was stirred at ambient temperature for 70 h, added a saturated aqueous solution of ammonium chloride and the phases separated. The aqueous phase was extracted with dichloromethane (2×), and the combined organic phases were dried (Na$_2$SO$_4$), filtered and evaporated in vacuo. Flash chromatography on silica gel eluting with hexane/EtOAc (3:1) afforded 1.04 g (72%) of the title compound as a colourless solid.

S-Iodomethyl 6α,9α-difluoro-16α-elaidoyloxy-11β-hydroxy-16α-methyl-3-oxoandrosta-1,4-diene-17β-carbothioate

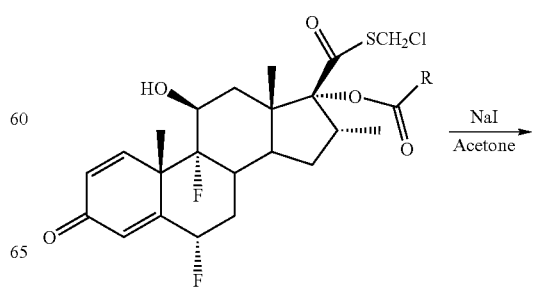

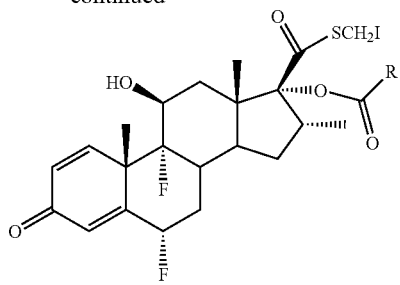

A solution of S-chloromethyl 6α,9α-difluoro-16α-elaidoyloxy-11β-hydroxy-16α-methyl-3-oxoandrosta-1,4-diene-17β-carbothioate (1.04 g, 1.4 mmol) in acetone (100 ml) was added sodium iodide (0.86 g, 5.7 mmol) and refluxed for 22 h. The solvent was evaporated in vacuo and the residue dissolved in EtOAc and washed with water, 10% aqueous solution of sodium hydrogen carbonate, water, dried (Na$_2$SO$_4$), filtered and evaporated in vacuo. The crude product (1.1 g) was used directly in the next step.

S-Fluoromethyl 6α,9α-difluoro-16α-elaidoyloxy-11β-hydroxy-16α-methyl-3-oxoandrosta-1,4-diene-17β-carbothioate

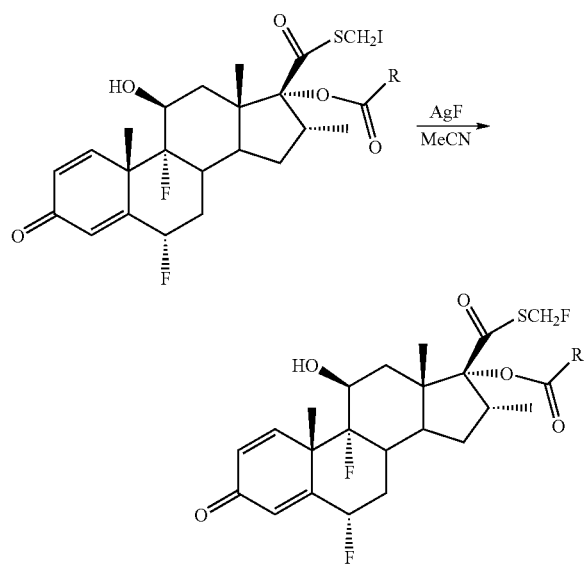

A solution of S-iodomethyl 6α,9α-difluoro-16α-elaidoyloxy-11β-hydroxy-16α-methyl-3-oxoandrosta-1,4-diene-17β-carbothioate (1.1 g, 1.35 mmol) in acetonitrile (65 ml) was added silver fluoride (1.7 g, 13.5 mmol) and stirred in the dark at room temperature for 40 h. The mixture was diluted with EtOAc and filtered through a short plug of celite and silica gel. The filtrate was washed with water, dried (Na$_2$SO$_4$), filtered and evaporated in vacuo. $^1$H NMR of the crude product revealed that some unreacted chloride was present, and the last two steps were repeated for fully conversion of the chloride to the fluoride. The product was then purified by flash chromatography on silica gel eluting with hexane/EtOAc (3:1) to give 0.65 g (46%, two steps) of the title compound as a colourless solid.

EXAMPLES

The examples below illustrate the present invention. These examples are, however, not to be construed as limitations of the scope of the present invention.

Example 1

The U937 and THP-1 cell lines were seeded, 20 000 cells per well, in 96-well-plates. 50 μl cell culture medium was added to each well. At the same time test compounds were added in 5 different concentrations and incubated for 48 hours. The CellTiter 96® Non-Radioactive cell proliferation assay (Promega) was used to study the cytotoxicity of test compounds in these cells. This assay is a colorimetric method for determining the number of viable cells in proliferation or chemosensitivity assays. It is composed of solutions of a novel tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent (phenazine methosulfate; PMS). MTS is bioreduced by cells into a formazan product that is soluble in tissue culture medium. The absorbance of the formazan at 490 nm can be measured directly from 96 well assay plates without additional processing. The quantity of formazan product as measured by the amount of 490 nm absorbance is directly proportional to the number of living cells in culture (IC$_{50}$ values). The test compounds were fluticasone propionate and fluticasone elaidic acid derivative. In this glucocoricoid resistant cell lines, fluticasone elaidic acid was highly potent with IC$_{50}$ values in the micromolar range, the U937 cells being the most sensitive.

TABLE 1

| Compound | U937 cells, IC$_{50}$ μM ± SD | THP1 cells, IC$_{50}$ μM ± SD |
| --- | --- | --- |
| Fluticasone propionate | >100 μM ± 0.03 | >100 μM ± 0.02 |
| Fluticasone elaidic acid derivative | 1 μM ± 0.02 | 10 μM ± 0.04 |

Example 2

Monkey kidney COS-1 cells (ATCC CRL 1650) were grown in Dulbecco's modified Eagle's medium (Gibco BRL, Grand Island, N.Y.) as described elsewhere (9). Transient transfections of COS-1 cells were performed as described elsewhere (10). The cells were plated at a density of 2×10$^5$ cells/well. Each well received 5 μg test plasmid, 5 μg β-galactosidase control plasmid as an internal control and either 2 μg expression plasmid, pMT-hGR or pGL3-basic as carrier. Plasmid details: The mouse PPARα gene is described elsewhere (11). Vectors expressing the LUC reporter gene under the control of the PPARα5'-flanking and promoter region were constructed in the pGL3-LUC vector (Promega). The PPARα 5'-flanking sequence between −2800 bp and +100 bp was cloned into NheI digested pGL3-LUC to generate the PPAR (−2800/+100) LUC plasmid Each transfection was performed in triplicates. The cells were transfected 24 h after plating together with fresh medium containing ligand. After 72 h cells were harvested, cytosol extracts were prepared and LUC activities were measured according to the Promega protocol. Results were normalized against β-galactosidase activities measured by incubating 100 μl extract with 0.28 mg o-nitrophenyl-D- galactoside (ONPG) in 50 mM phosphate buffer pH 7.0, 10 mM KCl, 1 mM MgCl$_2$ for 30 min at 30° C. and reading absorbance at 420 nm.

The test compounds were fluticason propionate, fluticasone elaidic acid derivative and flumethasone-elaidic acid ester derivative. The steroid compound, Fluticasone propionate was able to induce reporter gene activity by 100%, while surprisingly fluticasone elaidic acid ester derivative and flumethasone elaidic acid ester derivative only induced reporter gene activity by 15% and 2%, respectively. The steroid analogues were much less potent in gene activation of genes representing side effects.

TABLE 2

| Compound | luciferase activity/β-galactosidase (in percent (%) of Fluticasone propionate) |
|---|---|
| Fluticasone propionate | 100% |
| Fluticasone elaidic acid ester derivative | 15% |
| Flumethasone elaidic acid ester derivative | 2% |

Example 3

IL-1β-stimulation causes an increase in granulocyte-macrophage colony-stimulating factor (GM-CSF) release after 24 hours in A549 TRE (AP-1 regulation) cells. Inhibition of the GM-CSF release is measured after 24 hours exposure to a test compound. Fluticasone elaidic acid ester derivative, produced a concentration-dependent inhibition of IL-1β-stimulated GM-CSF release in A549 TRE cells with an IC$_{50}$=1.4×10$^{-11}$M. Fluticasone propionate produced a concentration-dependent inhibition of GM-CSF release in A549 TRE cells of IC$_{50}$ 3.1×10$^{-10}$M (Table 3). The fluticasone elaidic acid ester derivative was 22 times more potent in the inhibition of GM-CSF release, that is 22 times more potent anti-inflammatory action in this assay.

Induction of GRE-luciferase activity was observed in stably transfected A549 GRE-luciferase cells. No effect on GRE-luciferase activity was seen in A549 GRE-luciferase cells compared to a concentration dependent induction of GRE-luciferase reporter activity in A549 GRE-luciferase cells exposed to fluticasone propionate which caused a maximum stimulation of luciferase activity of EC50=5.1× 10$^{-10}$ M.

Surprisingly the inhibition of GM-CSF is increased more than 20 fold for the fluticasone elaidic acid ester derivative compared to a lack of effect on the GRE-luciferace. Indicating a higher therapeutic index also in this test system.

TABLE 3

| Steroid | A549 TRE (+IL-1β) IC$_{50}$ |
|---|---|
| Dexamethasone | 8.5 × 10$^{-10}$M |
| Fluticasone-propionate | 3.1 × 10$^{-10}$M |
| Fluticasone elaidic acid ester derivative | 1.4 × 10$^{-11}$M |

REFERENCES

1. Genome-wide identification of prednisolone-responsive genes in acute lymphoblastic leukaemia cells., Tissing W. J. et al., Blood, 2007 Jan. 11
2. Identification of budesonide and prednisolone as substrates of the intestinal drug efflux pump P-glycoprotein., Dilger K. et al. Inflamm. Bowel Dis. 2004 Sep. 10 (5): 578-83.
3. Mechanisms of steroid action and resistance in inflammation., I. M. Adcock and S. J. Lane, J. of Endocrinology (2003) 178, 347-355.
4. Anti-inflammatory actions of glucocorticoids: Molecular mechanism., Barnes et al. (1998) J. Clinical Science 94, 557-572.
5. Inhaled corticosteroids: past lessons and future issues, Allen D. B. et al., J. Allergy Clinic. Immunol. 2003; 112, p. 1-40.
6. Designing corticosteroid drugs for pulmonary selectivity.; K. Biggadike, I. Uings and S, N. Farrow; Proceedings of the American Thoracic Society, Vol 1, p. 352-355, 2004.
7. Sulfasalazine sensitizes human monocytic/macrophage cells for glucocorticoids by up-regulation of receptor (alpha) and glucocorticoid-induced apoptosis., Oerlemans R. et al., Ann. Rheum. Dis., 2007 Jan. 31.
8. GM-CSF in inflammation and autoimmunity, Hamilton J. A., Trends Immunol., 2002 Aug. 23(8); 403-8.
9. Establishment of a clonal strain of hetatoma cells which maintain in culture the five enzymes of the urea cycle. Richardson U. I., Snodgrass P. J., Nuzum C. T., Tashjian A. H., Jr. (1974) J. Cell Physiol. 83: 141-149.
10. A new technique for the assay of infectivity of human adenovirus 5 DNA, Graham et al. 1973) Virology 52: 456-467.
11. Structure of the mouse peroxisome proliferator activated reporter gene. Gearing et al. (1994) BBRC 199, 255.
12. Reversible formation of fatty acid esters of budesonide, an antiasthma glucocorticoid, in human lung and liver microsomes. Tunej, A. Sjodin, K. and Hallstrom, G., Drug Metabolism and Disposistion, 25(11); 1311-7 (1997)

The invention claimed is:
1. A compound defined as:

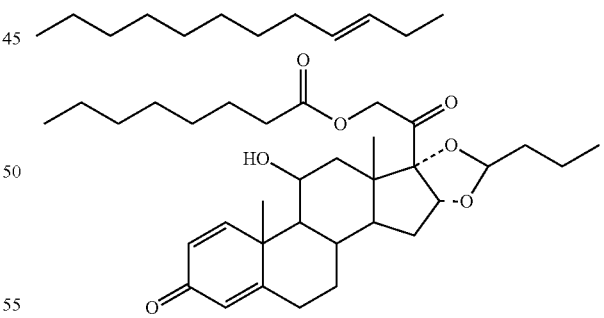

2. A pharmaceutical composition, comprising a compound as defined in claim 1, and pharmaceutically acceptable excipients, carriers and/or diluents.

* * * * *